US00RE34938E

United States Patent [19]

[11] E Patent Number: Re. 34,938

Serikov et al.

[45] Reissued Date of Patent: May 16, 1995

[54] NON-INVASIVE METHOD FOR MEASURING LUNG TISSUE VOLUME AND PULMONARY BLOOD FLOW AND A PROBE TO CARRY OUT THE METHOD

[76] Inventors: Vladimir Serikov, Shvernic Ave., Bldg. 51, Apt. 51, St. Petersburg, 194021; Mark Rumm, Blohina St., 23-3, St. Petersburg, 197198, both of Russian Federation; Norman C. Staub, University of California, San Francisco, School of Medicine, Cardiovascular Research Institute, M-1327, Box 0130, San Francisco, Calif. 94143-0130

[21] Appl. No.: 46,403

[22] Filed: Apr. 9, 1993

Related U.S. Patent Documents

Reissue of:

[64] Patent No.: 5,005,582
Issued: Apr. 9, 1991
Appl. No.: 545,031
Filed: Jun. 28, 1990

[51] Int. Cl.[6] ..... A61B 5/0205

[52] U.S. Cl. ..... 128/691; 128/716; 128/719; 128/724; 128/725

[58] Field of Search ..... 128/691, 716, 719, 724, 128/725

[56] References Cited

U.S. PATENT DOCUMENTS

| | | | |
|---|---|---|---|
| 3,347,224 | 10/1967 | Adams . | |
| 3,359,974 | 12/1967 | Khalil . | |
| 3,798,967 | 10/1972 | Gieles | 128/692 |
| 3,962,917 | 6/1976 | Terada | 128/724 |
| 4,024,873 | 5/1976 | Antoshkiw | 128/713 |
| 4,230,126 | 11/1978 | Elings | 128/671 |
| 4,329,993 | 6/1990 | Lieber | 128/691 |
| 4,444,201 | 4/1984 | Itoh | 128/725 |
| 4,488,559 | 6/1981 | Iskander | 128/653.1 |
| 4,567,888 | 2/1986 | Robert et al. | 128/724 |
| 4,802,439 | 7/1987 | Nitzan | 128/691 |
| 4,802,490 | 2/1989 | Johnston | 128/661.08 |
| 4,830,022 | 5/1989 | Harshe et al. | 128/724 |
| 4,914,720 | 4/1990 | Knodle et al. | 128/719 |

OTHER PUBLICATIONS

Casaburi, R., K. Wasserman and R. M. Effros, Detection and Measurement of Pulmonary Edema. In: Lung Biology in Health and Disease. Lung Water and Solute Exchange, ed. N. C. Staub, New York, M. Dekker, 1978, vol. 7, Chapter 11, pp. 323-377.

*Primary Examiner*—George Manuel
*Attorney, Agent, or Firm*—Ronald M. Anderson

[57] ABSTRACT

This is a non-invasive method for measuring pulmonary blood flow and lung tissue volume, called airway thermal volume consisting of dynamic registration of respiratory heat losses in ventilatory loading and/or humidity and temperature changes of the inspired gas. Pulmonary blood flow and airway tissue volume are calculated by solving the differential equation for nonsteady-state heat and mass exchange between the lungs and the environment. The lungs fraction as natural conditioner of the inspired air, having an inner heat source (pulmonary blood flow) and an outgoing heat stream calculated by measuring the volume ventilation and the temperature and humidity of inspired and expired air. Alterations of the baseline steady-state condition of lung respiratory heat exchange with the environment by changes in ventilation lead to achievement of a new steady-state condition where the heat stream from the lungs into environment is balanced by the heat stream from the circulation into the lung tissue. The maximal temperature of the expired air is taken as an initial relative value of lung tissue temperature, so that the quantity of maximal expired temperature change between two different steady-state conditions of lung heat exchange is proportional to the pulmonary blood flow, while the rate at which the new steady-state is achieved is proportional to the quantity of tissue mass. A probe for carrying out measurements includes a low-inertial device for temperature and humidity measurements of the expired and inspired air located in the middle of the airstream near the entrance to the upper respiratory tract, combined with a device for gas volumetric measurements and valves dividing in- and outflowing air for minimizing errors in air temperature and humidity measurements.

3 Claims, 6 Drawing Sheets

NON-INVASIVE METHOD FOR MEASURING LUNG TISSUE VOLUME AND PULMONARY BLOOD FLOW AND A PROBE TO CARRY OUT THE METHOD

Matter enclosed in heavy brackets [ ] appears in the original patent but forms no part of this reissue specification; matter printed in italics indicates the additions made by reissue.

FIELD OF THE INVENTION

This invention generally relates to the methods and apparatus employed to measure regional blood flow and tissue mass; more particularly to measurements of cardiac output and lung edema.

BACKGROUND OF THE INVENTION

Assessments of fluid volume of the lung, as well as determination of cardiac output, are of importance for clinical medicine and physiological research. Acute respiratory insufficiency is a major cause of mortality in patients, being commonly a complication of various disturbances in lung fluid balance leading to the development of pulmonary edema. The latter can be caused by a number of factors and its appropriate treatment requires adequate diagnosis and early therapy.

Both direct and indirect methods for assessing the fluid volume of the lungs have been developed and thoroughly investigated for their potential significance and accuracy in clinical and experimental research. Generally only indirect, or non-distructive measures can be applied in clinical investigations, although they are not so accurate as direct ones. Among the indirect measurements are: lung mechanics and pulmonary gas exchange, non-gaseous and gaseous indicator-dilution procedures, measurement of transthoracic impedance and radiological methods. All of these, based on different physical principles of measurement, have specific limitations, for theoretical and methodologic reasons.

Lung mechanics are changed in edema due to progressive engorgement by edema fluid, which decreases lung compliance and increases resistance to airflow. But, these changes are not specific for edema, being caused also by changes in alveolar surface tension or vascular hypertension. Also, non-specific changes in lung mechanics due to bronchoconstriction can alter the results significantly.

Gas exchange disturbances usually occur in lung edema. However, these disturbances are also non-specific and provide information more of a qualitative, than of a quantitative nature. Being influenced by numerous variables of ventilation and perfusion, anatomical and physiological shunting and various feedback regulatory mechanisms gas exchange disturbances are of importance mainly for the detecting final alveolar flooding stage of pulmonary edema.

Radiological methods are mostly of a semi-quantitative character, based on special radiographic criteria and are not likely to provide objective or fast monitoring information, although it is the most widely available pulmonary edema diagnostic procedure. Utilizing others kinds of external energy sources, for example, microwave sources and corresponding detectors (U.S. Pat. No 4,488,559, Iskander M.) also does not provide enough accuracy and quantitiveness for lung water measurements.

As lung tissue is a conductor of electric current and lung conductivity vanes strikingly with inflation and water content of lung tissue, changes in transthoracic impedance can be used for the lung water measurements. Limitations of this method are in the inability to distinguish conductivity of the lung itself from the surrounding tissue (chest wall), low sensitivity, demands of stable chest geometry and electrode positioning and inability to determine absolute values.

Indicator dilution procedures are most commonly used for quantitative measurements of lung water content. Indicators are injected intravascularly and indicator concentrations are measured in the systemic arterial blood or by external probes in the case of gamma-emitting isotopes. Two indicators: one non-permeable (vascular reference) and the other permeable (extravascular reference) are utilized. The vascular reference indicator remains confined to the vascular volume, while the permeable indicator readily diffuses into the extravascular compartment of the lung.

For the extravascular reference tritiated water or heat seem to be most appropriate, having the highest diffusion coefficients. Reference, for example, U.S. Pat. No. 4,230,126, Elings V. From the time-course of both indicators appearance and concentration in systemic arterial blood, it is possible to calculate the blood flow through the lung (vascular reference) and extravascular water content using the mean transit time difference between both indicators. These methods are well grounded by mathematical analysis of the processes of non-study-state transfer of indicators in the fluid stream and its exchange with surrounding tissues. There are different mathematical and technical approaches to performing the measurements and calculating the results. Such details as injection site and form, methods of indicator collection and detection, as well as the site of collection may substantially influence the results. Adequate measurements require appropriate mixing of indicator at the entrance and exit of the lung, correction for the delay imposed by the collection catheter and the position of the collection catheter. In the ideal situation the collection catheter would be located in the left atrium, but that involves additional technical problems in positioning the catheter.

The principal theoretical limitation of the method is the perfusion-dependant distribution of the extravascular indicator. If some portions of the lungs are poorly perfused, as is often true in lung diseases, it is difficult to obtain correct mean transit times due to incomplete recovery of tracer (flow limited). Recirculation of indicator is another serious problem because the slowly perfused portions of the lung may empty during the period of recirculation. Improper extrapolation of the indicator-dilution curve downslope is the reason why standard indicator dilution curves measure only a fraction of 40–90% of the lung thermal mass. Since lung tissue is composed of different types of organic materials, the solubility of indicators in water and lipids is important. For example, different permeable indicators yield different extravascular volumes (diffusion limited), Further, the main problem preventing its wide clinical use is the invasiveness of the procedure. Most techniques require positioning of catheters for indicator injection and collection in the pulmonary artery and aorta respectively. Catheterization of the heart, especially puncturing of a large artery are complicated procedures, often accompanied by various complications -clotting, embolism etc., and can not be recommended as routine procedures. Positioning of the probes outside the chest without direct contact with the arterial bloodstream significantly decreases the accuracy of the measurements.

The above-mentioned drawbacks can be eliminated by using high-energy indicators and external scanning over the chest. Scanning procedures may permit more accurate evaluation of poorly perfused regions and retention of the indicator, as well as measurements of regional water content. Such determinations of lung water with the gamma-indicator $^{22}$-Na were used by Weidner in 1956, and by Kety's (1949) measurements of tissue perfusion. This procedure never became clinically popular because of considerable exposure to radioactivity and uncertainty regarding tracer distribution in cells. Others indicators, such as $^{99}$Tc-DTPA are being currently used. As this indicator is extracellular, it is not possible to distinguish between the plasma and interstitial water volumes. Uncertainty regarding the contribution of thoracic wall activity exists. The method also requires employing of expensive and sophisticated apparatus.

A different approach is used in methods utilizing soluble gas absorption by the lung tissue. Such measurements of lung tissue volume have been studied, since Cander and Forster used the inert gas acetylene for this purpose in 1959. The method is based on measuring the concentration of exhaled soluble gas after inhalation of a gas mixture with known concentration of the test gas. The soluble gas disappears from the airways and alveolar spaces due to its solution in lung tissues and blood. Constant blood flow via the lungs provides continuous extraction of the test gas from the lungs, so that pulmonary blood flow is also determined in these measurements. The solubility of the gas is of critical importance for the determination of lung water.

One of the main limitations of the soluble gas technique involves the back extrapolation of the disappearance curve to zero time of the soluble gas following multiple breathholds of the test-gas mixture. These back-extrapolation calculations are sensitive to a variety of measurement errors. Some factors which might occasion systematic errors are: cardiac output changes during the breathhold maneuvers, inhomogenities in the lung ventilation/perfusion ratios an inhomogenities of the lung deflation pattern. Also the method is sensitive to alterations in ventilation distribution which can be critical in pulmonary edema due to airway closure.

Application of the technique demands expensive and accurate apparatus for precisely measuring the gas concentration such as a mass spectrometer. Also the method is not useful in very sick patients, because the procedure requires rather complicated breathing procedures with the special gas mixture.

Although this method is capable of providing accurate enough measurement of lung water and cardiac output, the complexity and expense of the related gas concentration processing apparatus has significantly limited its widespread commercial application.

Various methods have been proposed for the measurement of cardiac output or pulmonary blood flow alone, without measuring lung water content. Most of them are also invasive, employing intravascular catheters or probes. The pioneering method was by Fick (1870), which was based on the measurement of oxygen consumption and the arterial-venous $O_2$ concentration difference. But the method requires obtaining arterial and mixed venous blood samples. Single indicator dilution methods are also used for blood flow determination. These are referred, for example, to U.S. Pat. Nos. 4,024,873, Antoshkiw et at., 4,329,993, Lieber et al.

Other invasive methods use different principles of fluid flow measurement-measurement of the differential temperature that results from localized heating of the blood (U.S. Pat. Nos. 3,359,974, Khalil, 3,798,967, Gieles et al.), electromagnetic energy (U.S. Pat. No. 3,347,224, Adams) or ultrasonic devices (U.S. Pat. No. 4,802,490, Johnston), or local heating or cooling of the tissue itself (U.S. Pat. No. 4,802,489, Nitzan). All these methods tend to be invasive, which is their main disadvantage.

It is therefore, the principal object of the new invention to provide a non-invasive method for pulmonary blood flow rate determination and pulmonary tissue volume determination, using heat as the permeable indicator of lung tissue volume and permitting non-invasiveness of the measurement. The method depends upon the lung'ability to humidify and heat the inspired air to the lung's own temperature over a wide range of breathing conditions, and upon easily performed measurements on expired air.

SUMMARY OF THE INVENTION

This invention provides a method (hereafter reffered to as airway thermal volume) for carrying out pulmonary tissue volume and pulmonary blood flow measurements, comprising the steps of:

1. Providing a probe for simultaneous measurement of temperature, humidity and volume flow of inspired and expired air and adapted to produce a signal indicative of temperature, humidity and gas flow at the entrance to the upper respiratory tract;

2. Measuring the temperature of the body;

3. Measuring the above mentioned variables in steady-state period of spontaneous or artificially-provided breathing, then changing the rate of breathing and/or temperature and humidity of inspired air, following the changes in temperature and humidity of expired air until new steady-state conditions are established under the new constant state of ventilation pattern;

4. Calculating pulmonary blood flow and airway thermal volume by integration of the differential equation of lung heat exchange with the environment by the known parameters of inspired gas temperature and humidity, measured expired gas temperature and humidity and taking mean-integrated temperature of the lung tissue as linearly proportional to the expired air temperature with a coefficient of proportionality that equals to the ratio of body temperature to the expired gas temperature at the beginning of the measurement.

BRIEF DESCRIPTION OF THE DRAWINGS

The invention will now be described in connection with certain preferred embodiments with reference to the following illustrations so that it may be more fully understood.

With specific reference to the figures in detail, it is stressed that the particulars shown are by way of example and for purposes of illustrative discussion of the preferred embodiments of the present invention only and are presented in the course of providing what is believed to be most useful and readily understood description of the principles and conceptual aspects of the invention. In this regard no attempt is made to show structural details of the invention in more detail than is necessary for a fundamental understanding of the invention; the description taken with the drawings making apparent to those skilled in art how the several forms of the invention may be embodied in practice.

In the drawings

FIG. 1 represents the scheme of heat exchange in the lung;

FIG. 2 represents a typical temperature-time curve of the expired air during lung ventilation with dry air at a ventilation rate three times greater than baseline;

FIG. 3 represents curves of the expired air temperature-time in ventilatory loading for various lung tissue mass;

FIG. 4 represents curves of the expired air temperature-time in ventilatory loading for various pulmonary blood flow;

FIG. 5 represents the method of analysing of the parameters of the curve;

FIG. 6 represents a general set up of the probes for measuring temperature, humidity and ventilation.

DETAILED DESCRIPTION OF THE PREFERRED EMBODIMENTS

The temperature and water vapor concentration of the inflowing airstream differ from those at the mucosal surface of the respiratory tract. The respiratory tract adjusts the inspired air temperature and humidity as it conditions the inspired air nearly to body temperature and full humidification. As a result of this process the respiratory tract surface loses heat and water to the inspired air. Some part of the losses is recovered during expiration because condensation of water vapor occurs on the cooled surface of the bronchial tree. The amount of heat and water recovered is dependent on lowering of the temperature and water vapor concentration of the expired air. Due to heat exchange between the bronchial walls and the inspired air the walls of the bronchial tree and lung tissue are cooled. At the same time, a temperature gradient develops between the airway surfaces and blood vessels, so that heat streams from the blood to the tissues. In this manner pulmonary blood flow plays the role of an inner heat source for the lungs.

Figure 1:
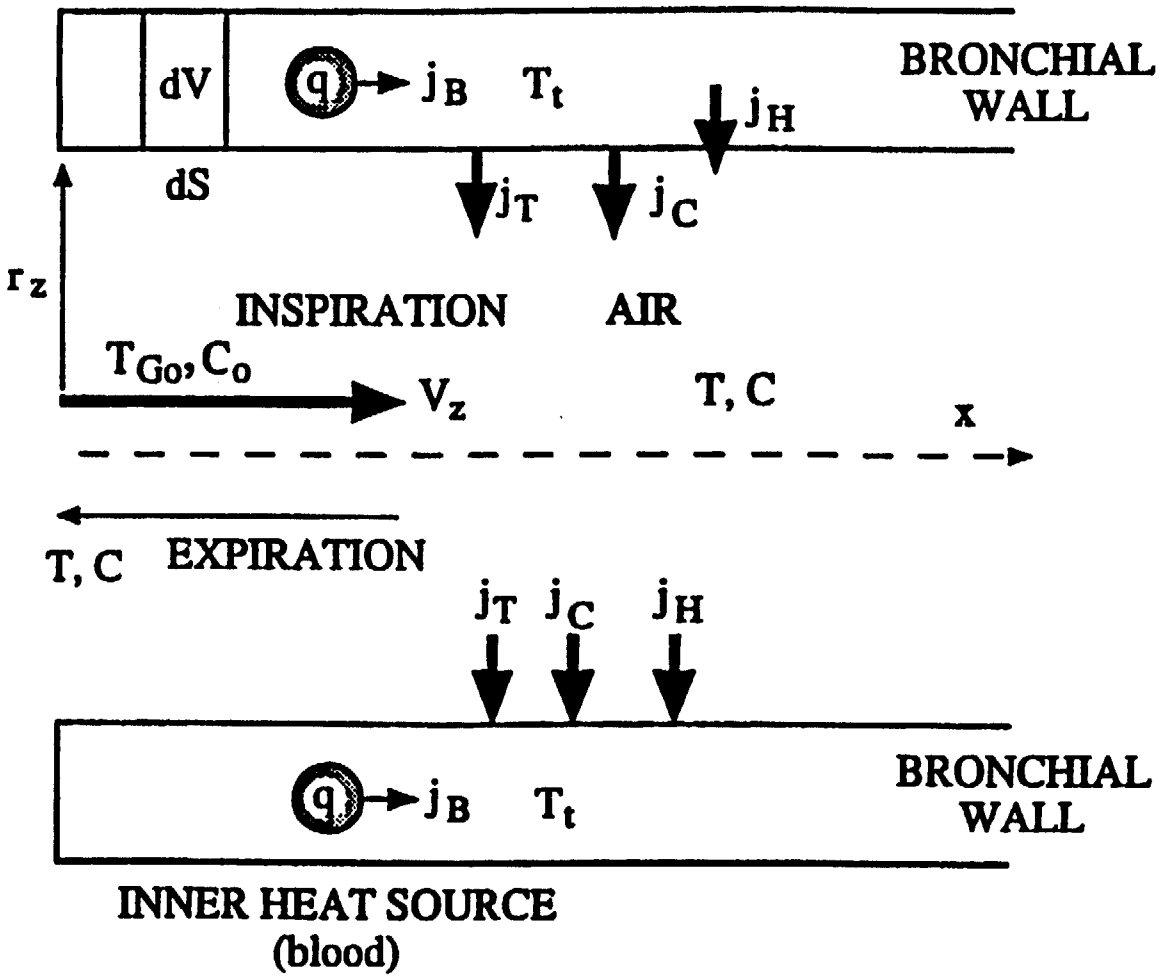

Referring now to the drawings, the scheme of heat fluxes in the lung tissue is given in FIG. 1, for inspiration and expiration. An element of lung tissue of volume, dV, and related to the contact with air surface area element, dS, having temperature, $T_t$, provides two different heat fluxes into the incoming airstream with air temperature, $T_{Go}$, and water vapor concentration, $C_o$, during inspiration. The first one, jT, is the convectional and dissipative heat flux, associated with water vapor transfer, jC, from the bronchial surface into the airstream, and the latter can be given as:

$$jC = U_2,(dC/dx)/r_2 = 2\,b(C_w - C), \quad (1)$$

where $U_z$ is the linear air velocity at a given point of the bronchial tree, C is the water vapor concentration, x is the length coordinate of the bronchial tree, $r_z$ is the radius of the bronchus, b is the coefficient of water vapor mass transfer from the wall, $C_t$ is the concentration of totally saturated water vapor at the wall, and depends on the wall temperature.

Total convectional and dissipative heat flux can be given as:

$$jT = \rho_G C_{pG} U_z (dT/d\chi) r_z = 2(T_t - T)\,(a + jCC_{pw}), \quad (2)$$

where $\rho_G$ is the gas density, T is the gas temperature, $C_{pG}$ is the heat capacity of gas, $T_t$ is the tissue temperature, a is the coefficient of heat transfer, $C_{pw}$ is the heat capacity of water.

The second heat stream, jH, is associated with the evaporative heat losses and is given as:

$$jH = jCH, \quad (3)$$

where H is the heat of water vaporization.

The equation for the specific instantaneous heat transfer to the lung tissues from the pulmonary circulation (the inner heat source) is given:

$$jB/S = K_t \rho_W C_{pt} q(T_B - T_w) + C_{pw} T_{Bq0} \rho_w, \quad (4)$$

where jB is the heat flux to the lung tissue from the pulmonary blood flow, $K_T$ *is the coefficient of lung tissue heat conductivity*, $\rho_w$ is the density of lung tissue, q is the pulmonary blood flow, $T_B$ is the temperature of blood, $q_o$ is the net fluid flux of water evaporated into the airstream.

The differential equation for the temperature balance of the lung tissue is given as the sum of these fluxes:

$$dV\rho_w C_{pt}(dT_t/dt) = \int (jB - jT - jH)dS, \quad (5)$$

where t is the time.

The above equations represent the mathematical model of lung heat exchange with the inspired air during breathing. They were used as a basis for the development of the method of pulmonary blood flow and airway thermal volume measurements.

Experimentally the amount of heat lost by the lungs during a certain period of breathing ($Q_o$) can be measured knowing temperatures and humidities of inspired and expired air and the total mount of the air that enters the lungs. It can be presented as:

$$Q_o = \int dt \int dS\,(jT + jH),$$

For practical purposes it can be given as the sum of a finit-difference elements as:

$$-Q_o = V_G((T_{GO} - T)\,\rho_G C_{PG} + (T_{GO} C_{pw} C_o - TC_{pw} C) + (C_o - C)H), \quad (6)$$

where $V_G$ is the volume of gas that entered the lungs over the time t, $Te_{Go}$ and T are the mean temperatures of inspired and expired gas, $C_o$ and C are the mean mass concentration of water vapor in inspired and expired air, respectively (here "mean" relates to the average value during one breathing cycle). All the above-mentioned parameters can be easily measured so that $Q_o$ can be determined explicitly.

During ventilatory loading of the lungs and/or changes in temperature and humidity of expired air, $Q_o$ will be changing as well as T. $Q_o$ and T will be the functions of time due to the cooling of the lung caused by increased outward heat flux until a new steady-state condition between heat loss into the environment and inner heat source (pulmonary blood flow) will be achieved. The corresponding equation of lung tissue cooling, taking into account eq. (5), can be given as:

$$V\rho_w C_{pt}(dt_t/dt) = q\rho_w C_{pt}(T_B - T_t) - Q, \quad (7)$$

where Q is net heat flux.

In order to determine the airway thermal volume, V, and pulmonary blood flow, q, we need to know the relationship between temperature of expired air, T, and actual mean-integrated temperature of lung tissue, $T_t$. This relationship can be given as a linear one:

$$T_t = K_R T, \tag{8}$$

where $K_R$ is the coefficient of proportionality and it is derived as:

$$K_R = T_B / T_o, \tag{9}$$

where $T_B$ is body temperature and $T_o$ is the temperature of expired air at the beginning of the ventilatory loading. In ventilatory loading the temperature of the expired air T will decrease to some steady-state value. In this new steady-state condition the heat losses to the expired air will equal the heat transfered from the pulmonary blood flow to the lung tissue:

$$(jT + jH) \int dS = jB \int dS = Q. \tag{10}$$

Eq. (10) allows one to calculate pulmonary blood flow in steady-state conditions.

Figure 2:
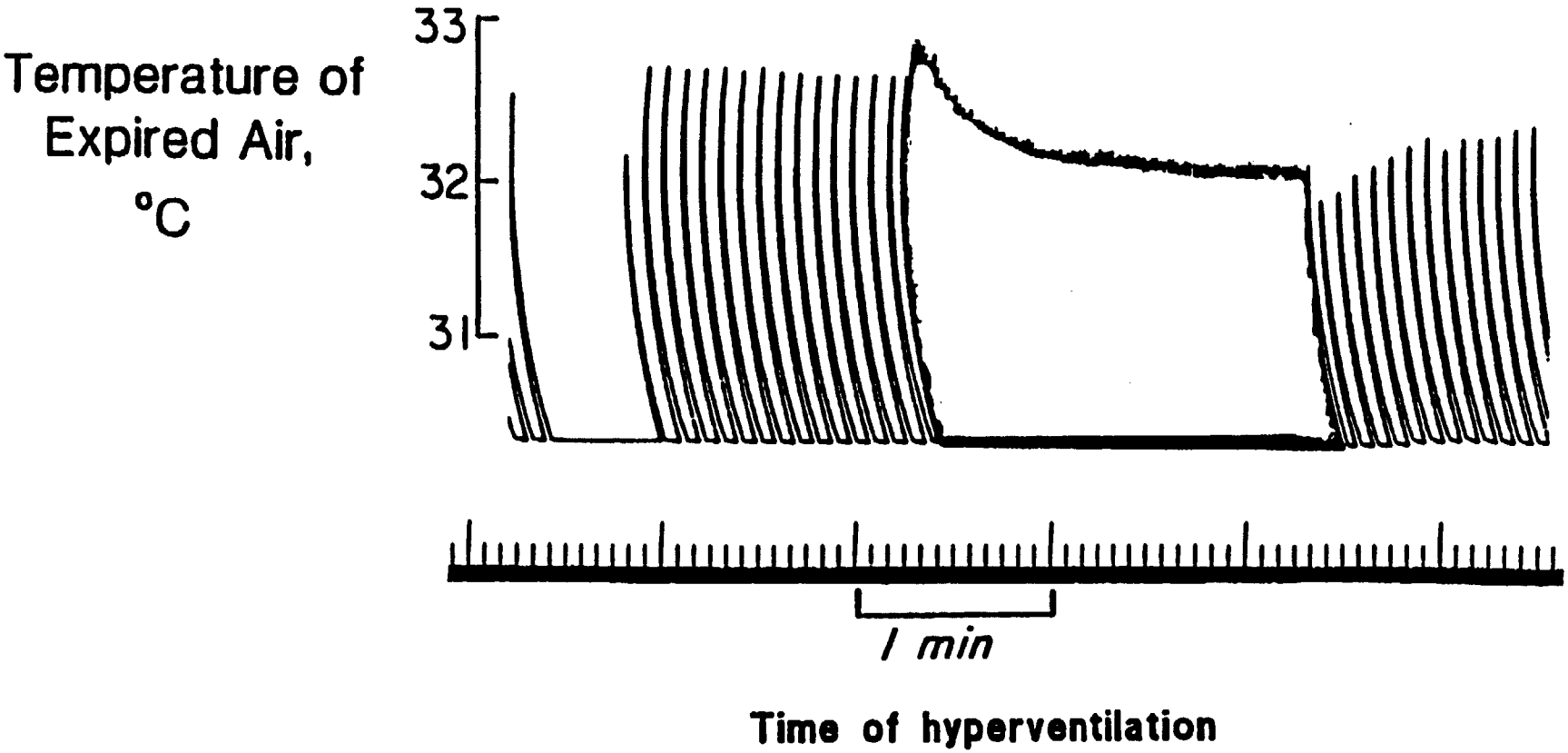

A typical curve of the expired air temperature-time curve during hyperventilation of a experimental animal is given in FIG. 2. The temperature of the expired air decreases monoexponentially during loading, reaching some steady-state condition of heat exchange.

Figure 3:
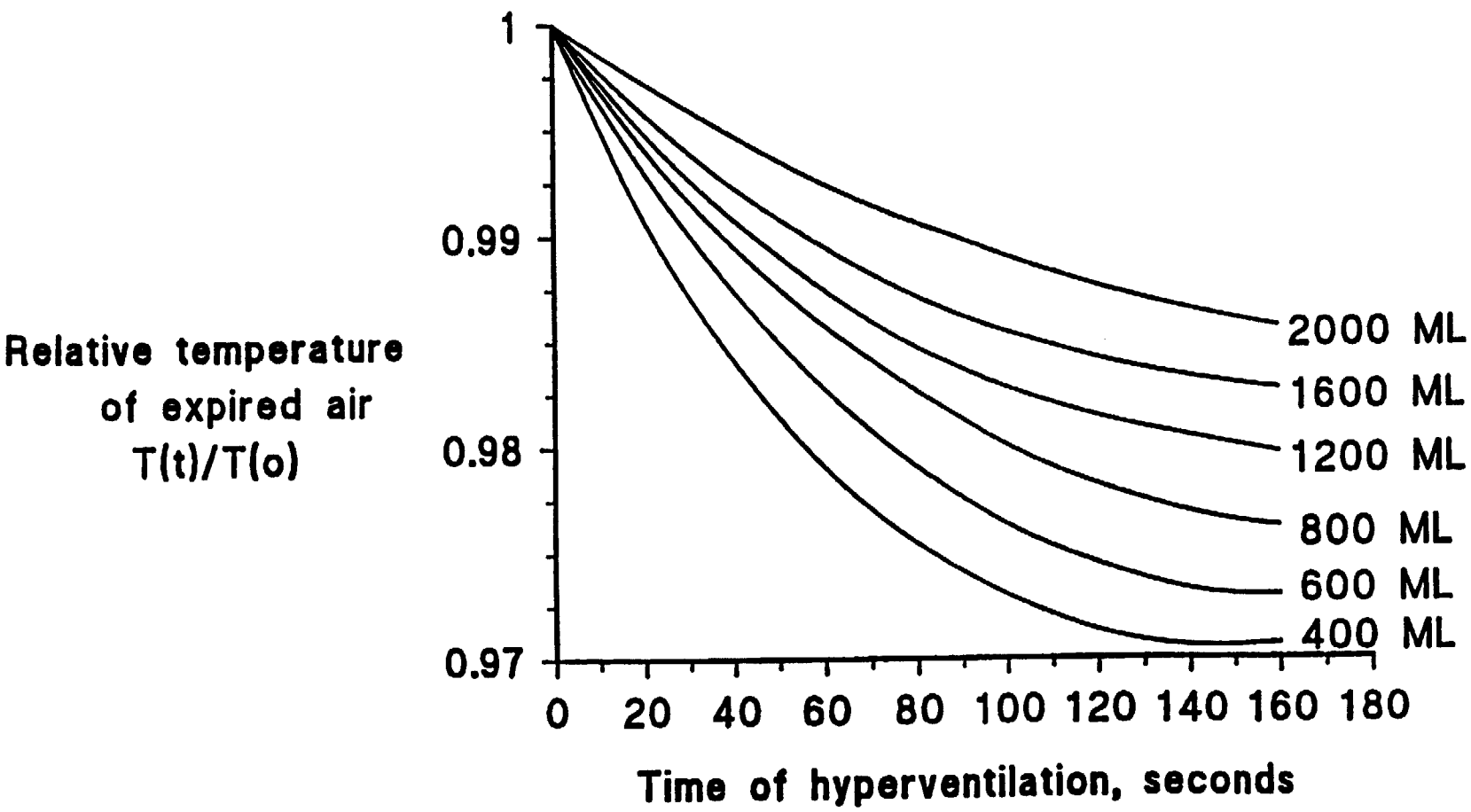

The developed model of lung heat exchange was analyzed to obtain predicted expired air temperature dynamics in situations where lung tissue volume or pulmonary blood flow change. In FIG. 3 the calculated values of the expired air temperature-time curve are given for different lung tissue masses, while the external heat losses and pulmonary blood flow were hold constant. Expired air temperature is given in relative values (actual temperature is related to initial temperature at the beginning of loading). As can be seen from the figure, increasing lung tissue mass is associated with distinct changes in the dynamics of the expired air temperature. The curve becomes smooth as V increases.

Figure 4:
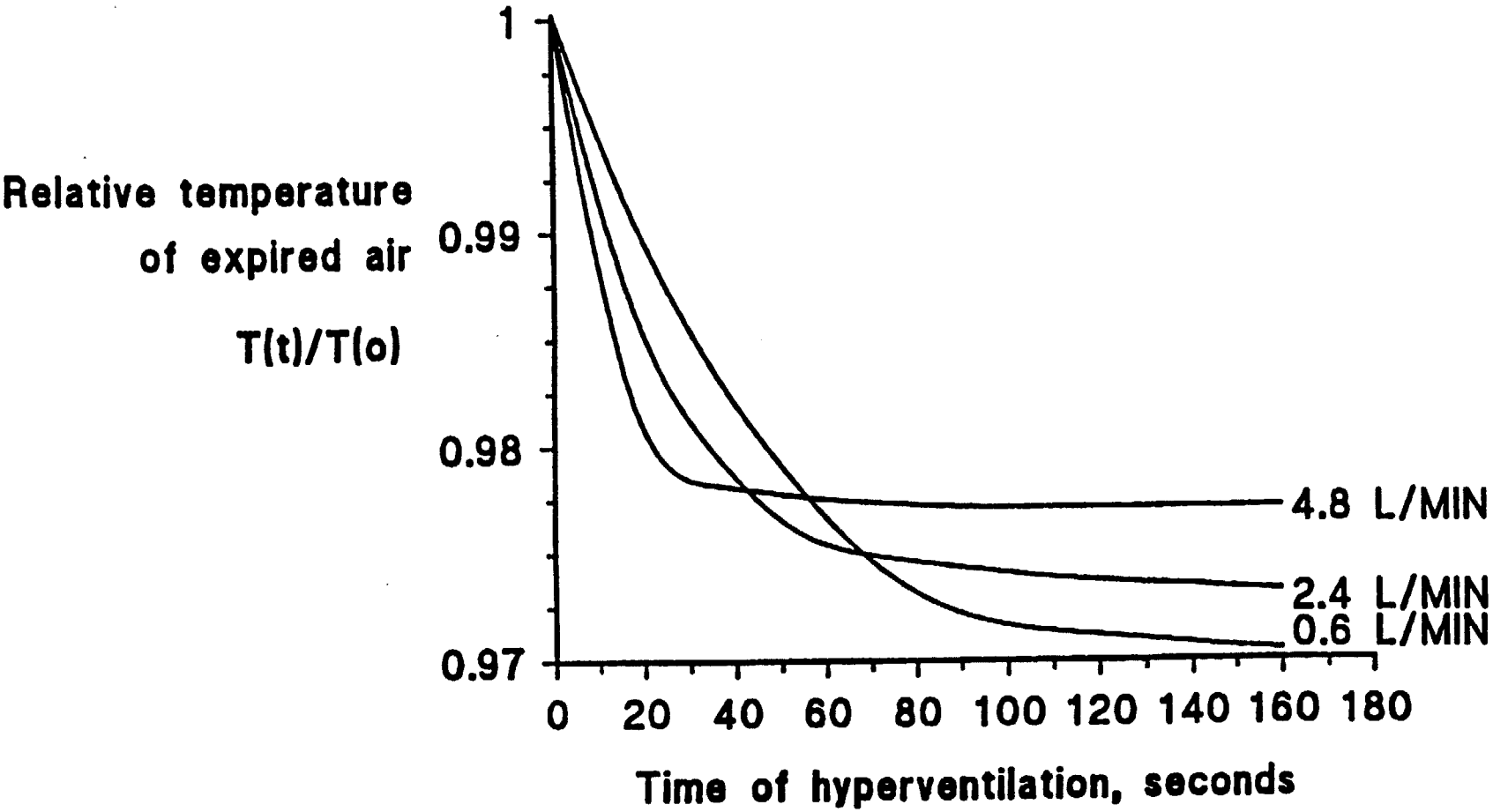

In FIG. 4 the expired temperature-time curve is analyzed in terms of pulmonary blood flow, while lung tissue mass and ventilation are constant. In this case the temperature of the final steady-state condition is markedly affected.

Convenient for practical purposes is the solution of eq. (7), which, by its analytical integration, enables one to obtain values of pulmonary blood flow, q, and airway thermal volume, V.

Practically the expired air from the lungs is always fully saturated at its temperature. This special case means that one does not have to measure both temperature and humidity of expired air but permits one to use only temperature for calculating heat loss, including evaporative heat losses, by calculating water vapor mass from the measured temperature of air.

For this purpose a linear approximation of the mass concentration of saturated water vapour in the air is used:

$$C(T) = 0.016 + 0.0018(T - 20), \tag{11}$$

where C is water vapor mass concentration ($kg/M^3$) and T is the temperature in degrees Centigrade. This linear approximation is valid for the temperature interval 20° to 38° C.

For this case eq. (7) can be given as:

$$dT/dt + AT + B = O, \tag{12}$$

where the constants A and B are:

$$A = qK_T/V + V_G\chi_1/VK_R + yH0.0018V_G/V\rho_w C\rho_w K_R, \tag{13}$$

$$B = (qT_B K_T/K_R V + V_G\chi_1 T_{GO}/VK_R + 0.02yHV_G/V\rho_w C\rho_w K_R)(-1), \tag{14}$$

where y is equals unity with dimension $kg*m^{-3}*K^{-1}$, $\chi_1$ is a dimensionless parameter $= (\rho_G C_{pG} + \rho_w C_{GO})/\rho_w C_p W$.

The density and heat capacity of lung tissue were taken as those of water ($\rho_w$ and $C_{pw}$ respectively).

The solution of eq. (12) can be easily obtained as:

$$T(t) = T_o \exp(-At)1 + B/AT_o) - B/A. \tag{15}$$

Figure 5:
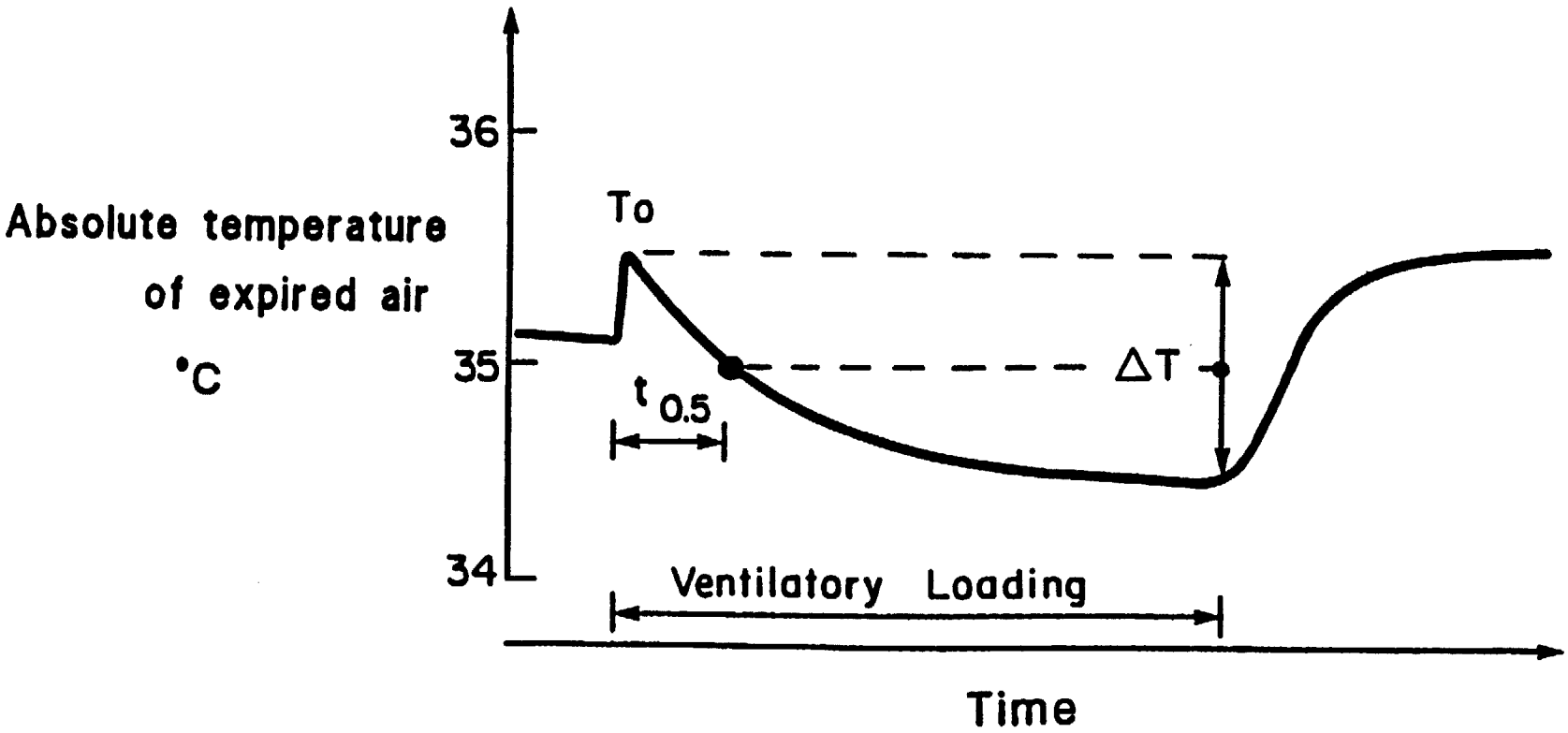

Equation (15) can be solved for two different steady-state conditions in terms of temperature fall, $\Delta T$—the difference of temperatures of expired air in two steady-states, and the half-time of the temperature fall, $t_{0.5}$. The graphic method for the evaluating of these parameters is given in FIG. 5.

Pulmonary blood flow, q, and airway thermal volume, V, are obtained from the curve of temperature dynamics vs time as:

$$q = V_G\chi_2(T_o - T_{Go} - \Delta T)/\Delta T K_T K_R, \tag{16}$$

$$V = t_{0.5}(qK_T K_R + V_G\chi_2)/0.69K_R, \tag{17}$$

where $\chi_2 = \chi_1 + 0.0018yH/\rho_w C_{pw}$.

In order to get particular values of pulmonary blood flow, q, and airway thermal volume, V, it is necessary to measure expired air temperature and humidity, body temperature during normal breathing and during ventilatory loading by changing the temperature and humidity of inspired, air and the following parameters or variables:

Temperature ($T_{Go}$) and humidity ($C_{Go}$) of inspired air
Temperature of the body ($T_B$)
Volume ventilation ($V_G$)
Initial temperature of expired air ($T_o$) and temperature fall ($\Delta T$) after reaching new steady-state
Half-time of temperature fall ($t_{0.5}$)

The other variables can be calculated from the above definitions and the relative coefficient of lung thermal conductivity, $K_T$, equals 0.2 (dimensionless).

Figure 6:
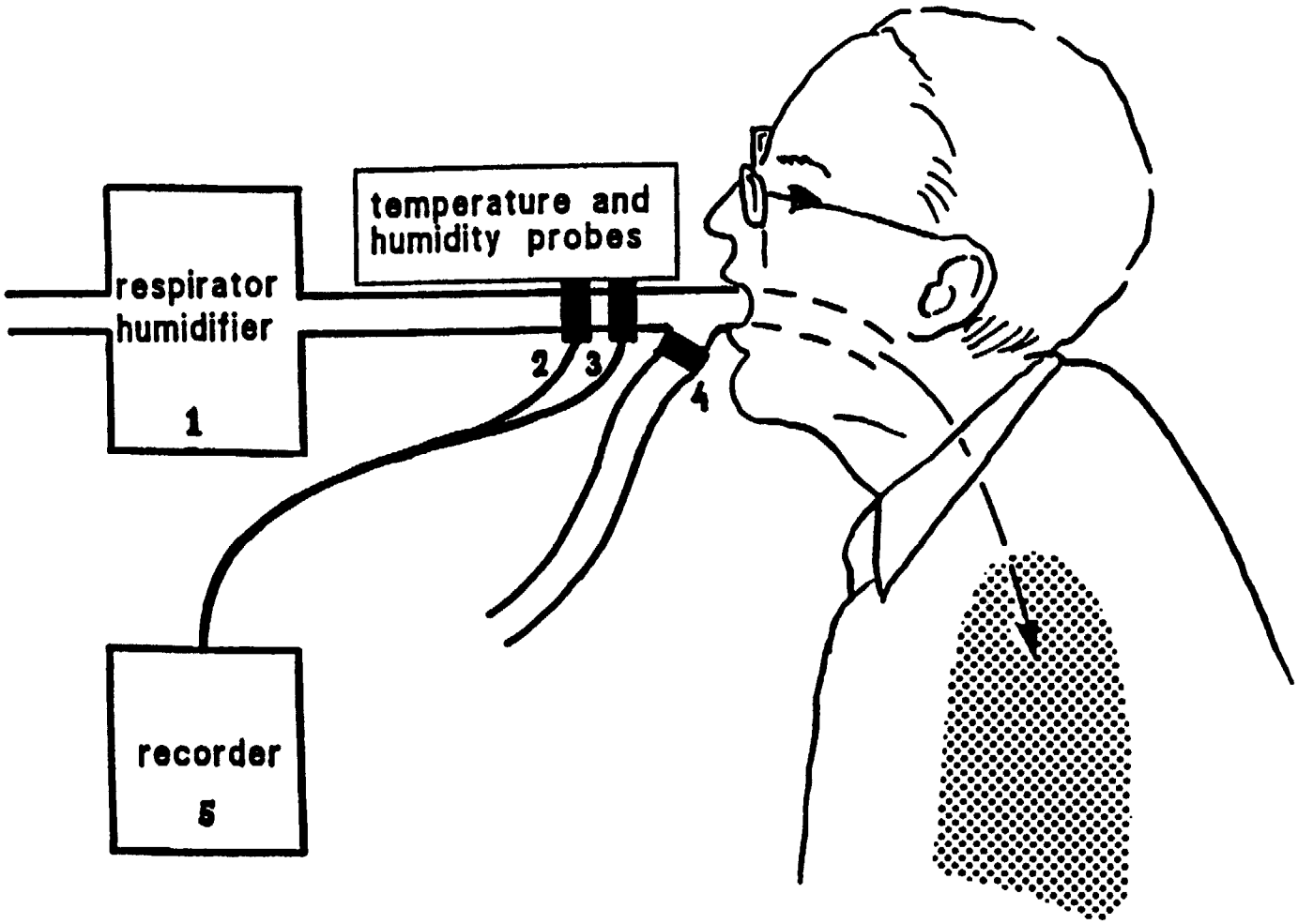

In FIG. 6 the general set-up of the probe for measurement of airway thermal volume is shown. The temperature probe for the expired air measurements should be positioned in the middle of the airstream. The probe should have a response time less than 0.05 sec and minimal mass to provide for accuracy of the airstream temperature measurement. The humidity probe should also be located in the middle of the airstream but should be positioned downstream to the temperature probe. For accurate measurements and to prevent water vapor condensation, the humidity probe is heated. Positioning of the humidity probe before the temperature probe may alter the temperature measurement. In most cases measurements of the expired air humidity is not necessary, assuming that the expired air is fully humidified. Although measuring this variable provides slightly more accurate measurements, it is associated with technical difficulties.

The ventilation measurement can be made at any point of the respiratory circuit, whereas the temperature and humidity probes should be located as close as possible to the upper respiratory tract entrance. Intubation tubing or tracheostomy can be succesfully used for this purposes in anesthetized humans or experimental animals.

The method and probe, according to the invention, are eminently suitable for automatic monitoring by connection to an analog-digital converter. Data can be stored in buffer memory and analyzed by a person or computer to obtain the variables needed for calculation of pulmonary blood flow and airway thermal volume.

For ventilatory loading, increasing the ventilation rate with a tidal volume of 22 ml/kg of body weight appends to optimal. Also hyperventilation ca be combined with using cold dry air which increases the heat loss. Either artificial ventilation or spontaneous breathing with air-$CO_2$ mixtures is satisfactory. The duration of altered ventilation depends on the subject and the rate of respiratory heat loss, ranging between 100–500 sec.

It will be evident to those skilled in the art that the invention is not limited to the details of the foregoing illustrative embodiments and that the present invention may be embodied in other specific forms without departing from the spirit or essential attributes thereof. The present description is therefore to be considered in all respects as illustrative and not restrictive, the scope of the invention being indicated by the appendant claims rather than by the foregoing description, and all changes which come within the meaning and range of equivalency of the claims are therefore intended to be embraced therein.

What is claimed is:

[1. A method for carrying out pulmonary blood flow and airway thermal volume measurements of a body, comprising the steps of:

providing measurements of temperature of inspired and maximal temperature of expired gas and gas volume flow (VG) at an entrance of the upper respiratory tract, humidity of said inspired gas and recording a curve of maximal expired gas temperature versus time measuring a temperature value ($T_B$) of said body, and measuring an expired gas initial temperature value ($T_O$) and an inspired gas temperature ($T_{Go}$) and inspired gas absolute humidity ($C_o$) value during an initial period of deep spontaneous or artificial breathing changing the rate of breathing with a tidal volume of breathing about 22 ml per kg body weight during a second period until steady-state lung heat exchange with constant maximal expired gas temperature is present determining from the temperature-vs-time curve a variable of temperature fall ($\Delta T$), and a half-time of temperature fall ($t_{0.5}$), and estimating pulmonary blood flow (q) and airway thermal volume (V) as a function of said temperature value ($T_B$), and said expired gas initial temperature value ($T_o$), and said inspired gas temperature ($T_{Go}$) and said inspired gas absolute humidity ($C_o$) and said variable of temperature fall ($\Delta T$) and said half-time of temperature fall ($t_{0.5}$) and said gas volume flow ($V_G$).]

[2. The method of claim 1 comprising the steps of:

providing cool dry gas mixture for said body to breathe such that said inspired gas temperature ($T_{Go}$) and said inspired gas absolute humidity ($C_o$) are cool and dry, respectively.]

[3. The method of claim 1 comprising the steps of:

providing a low-inertial humidity probe at the entrance of the respiratory tract of said body, and measuring simultaneously, an expired gas temperature value (T) and said inspired gas temperature ($T_{Go}$) and said inspired gas absolute humidity ($C_o$), and measuring a humidity (C) by means of said low-inertial humidity probe of said expired gas, and calculating said pulmonary blood flow and airway thermal volume iteratively by means of a differential equation of lung heat balance in non-steady-state as a function of said humidity (C) and said expired gas temperature value (T).]

*4. A method for making pulmonary blood flow measurements of a body, comprising the steps of:*

*(a) measuring a temperature of expired gas from a body;*

*(b) changing a rate of breathing of said body to vary its lung heat exchange;*

*(c) recording a curve of expired gas temperature versus time as the rate of breathing is changed;*

*(d) determining a time constant from the expired gas temperature versus time curve; and*

*(e) estimating a pulmonary blood flow rate as a function of said time constant.*

*5. A method for making pulmonary blood flow measurements of a body, comprising the steps of:*

*(a) measuring a temperature of expired gas from a body;*

*(b) changing a humidity of a gas mixture breathed by said body:*

*(c) recording a curve of expired gas temperature versus time as the humidity of the gas mixture breathed by said body changes;*

*(d) determining a time constant from the expired gas temperature versus time curve; and*

*(e) estimating a pulmonary blood flow rate as a function of said time constant.*

*6. A method for making continuous pulmonary blood flow measurements of a body, comprising the steps of:*

*(a) measuring a temperature and a gas volume flow of expired gas from a body;*

*(b) changing a humidity of a gas mixture breathed by said body;*

*(c) recording a curve of expired gas temperature versus time as the humidity of the gas mixture breathed by said body changes;*

*(d) determining a time constant from the expired gas temperature versus time curve; and*

*(e) periodically estimating a pulmonary blood flow rate as a function of said time constant, expired gas temperature, and said gas volume flow, said pulmonary blood flow rate being thereby estimated on a substantially continuous basis.*

* * * * *